(12) United States Patent
D'Amico et al.

(10) Patent No.: US 7,220,288 B2
(45) Date of Patent: May 22, 2007

(54) PROTECTION OF FRAGRANCE IN A WAX CANDLE USING AN ANTIOXIDANT

(75) Inventors: Daniel D'Amico, Tuckahoe, NY (US); Robert Black, New Rochelle, NY (US); Daniel Perlman, Arlington, MA (US); Richard Signorelli, Merrick, NY (US)

(73) Assignee: Belmay, Inc., Yonkers, NY (US)

( * ) Notice: Subject to any disclaimer, the term of this patent is extended or adjusted under 35 U.S.C. 154(b) by 0 days.

(21) Appl. No.: 10/217,899

(22) Filed: Aug. 13, 2002

(65) Prior Publication Data

US 2004/0031191 A1    Feb. 19, 2004

(51) Int. Cl.
*C10L 5/00*    (2006.01)

(52) U.S. Cl. .................................................. 44/275

(58) Field of Classification Search ................. 44/275; 431/288

See application file for complete search history.

(56) References Cited

U.S. PATENT DOCUMENTS

| | | | |
|---|---|---|---|
| 2,726,526 A * | 12/1955 | Walker | 431/288 |
| 3,091,952 A | 6/1963 | Black | |
| 3,630,697 A | 12/1971 | Durling et al. | |
| 3,645,705 A | 2/1972 | Miller et al. | |
| 3,844,706 A | 10/1974 | Tsaras | |
| 4,002,706 A * | 1/1977 | Pretorius | 264/13 |
| 4,110,261 A | 8/1978 | Newland | |
| 4,386,904 A | 6/1983 | Miyahara et al. | |
| 5,089,469 A | 2/1992 | Zampino et al. | |
| 5,171,329 A | 12/1992 | Lin | |
| 5,196,200 A | 3/1993 | Wilson et al. | |
| 5,879,694 A | 3/1999 | Morrison et al. | |
| 5,964,905 A * | 10/1999 | Camp et al. | 44/275 |
| 6,063,144 A | 5/2000 | Calzada et al. | |
| 6,066,329 A | 5/2000 | Morrison et al. | |
| 6,111,055 A | 8/2000 | Berger et al. | |
| 6,165,234 A | 12/2000 | Kanakkanatt | |
| 6,221,115 B1 | 4/2001 | Hyun et al. | |
| 6,224,641 B1 * | 5/2001 | Matzat et al. | 44/275 |
| 6,242,509 B1 | 6/2001 | Berger et al. | |
| 6,262,153 B1 | 7/2001 | Webster et al. | |
| 6,284,007 B1 | 9/2001 | Tao | |
| 6,296,674 B1 | 10/2001 | Trainer et al. | |
| 6,340,467 B1 | 1/2002 | Morrison | |
| 6,380,285 B1 | 4/2002 | Wood et al. | |
| 6,450,802 B1 * | 9/2002 | Steck | 431/288 |
| 6,544,303 B2 * | 4/2003 | Calzada | 44/275 |
| 6,706,081 B2 * | 3/2004 | Mack et al. | 44/275 |
| 2001/0013195 A1 | 8/2001 | Tao | |
| 2002/0032982 A1 | 3/2002 | Berger et al. | |
| 2003/0091949 A1 * | 5/2003 | Pesu et al. | 431/288 |

FOREIGN PATENT DOCUMENTS

JP    63214255    3/1987

OTHER PUBLICATIONS

21CRF172.515(Revised Apr. 1, 2003).*
Avon Products, 2000.*
Richard Signorelli, presentation, Apr. 2002.
U.S. Appl. No. 09/736,448, filed Aug. 29, 2002, Allison et al.
U.S. Appl. No. 09/728,132, filed Aug. 1, 2002, Calzada.
U.S. Appl. No. 09/950,404, filed Jun. 13, 2002, Wilson.
U.S. Appl. No. 09/729,181, filed Jun. 6, 2002, Steck.
U.S. Appl. No. 09/846,689, filed Feb. 28, 2002, Mack et al.
Robert H. Bedoukian, Peroxide Formation in Aroma Chemicals: The effect of Chemical Structure and Antioxidants on Product Integrity, presented at symposium, date unknown.

* cited by examiner

*Primary Examiner*—Cephia D. Toomer
(74) *Attorney, Agent, or Firm*—Buchanan Ingersoll & Rooney PC

(57) ABSTRACT

Disclosed is a fragranced wax candle and fragranced wax composition comprising paraffin wax, a fragrance containing an antioxidant, with or without vegetable wax and/or beeswax, saturated fatty acid, hindered amine, and an additive. Also disclosed is a method for incorporating an antioxidant into the fragranced candle wax composition.

3 Claims, No Drawings

PROTECTION OF FRAGRANCE IN A WAX CANDLE USING AN ANTIOXIDANT

FIELD OF THE INVENTION

The present invention pertains to a fragranced wax candle and especially to a fragranced candle wax composition comprising paraffin wax, a fragrance containing an antioxidant, optionally a vegetable and/or beeswax, saturated fatty acid, hindered amine and an additive. The present invention also pertains to a method for incorporating a fragrance containing an antioxidant into a candle wax composition containing varying amounts of paraffin wax. The instant candle wax composition protects the fragranced candle from undesirable changes occurring during its manufacture and during its burning, owing to the combination of heat, the presence of fragrance, and the requirement for ongoing capillary transport of wax upward in the wick of the candle.

BACKGROUND OF THE INVENTION

Candles have been known for many centuries, going back to the eighth century B.C. The nature of candles is described in Ulmann's Encyclopedia of Industrial Chemistry, Volume A5 at pages 29–30, where it is seen that candles are often made from paraffin, beeswax and stearin as basic materials, and where a host of other components and additives may also be present.

Paraffin-based candles that have been manufactured for many years contain non-renewable fuel sources including petroleum-derived paraffin and microcrystalline wax as well as other petroleum-based chemicals. These waxes may be mixed with a variable proportion of vegetable wax and/or beeswax, for example, soy wax or beeswax and saturated fatty acid such as a mixture of stearic and palmitic acid.

While candles containing renewable fuel sources such as vegetable wax and tallow are desirable and have been reported to burn with reduced emissions, such non-petroleum-based waxes are susceptible to discoloration in and near the melted wax pool and to reduced flame intensity associated with reduced capillary wax flow in the wick.

As candles of paraffin wax, vegetable wax, and mixed waxes became commercially important, efforts were made to "stabilize" said candles. At the National Candle Association meeting in Houston, 1994, R. van der Vennet presented a paper on "Antioxidants in Wax-Replacement of BHT" urging the use of Vitamin E (tocopherol) as an antioxidant to prevent the yellowing of wax when oxidized. This paper also describes the purpose of antioxidants, their mechanism, analysis, color and the maximum concentration of antioxidant for obtaining the best results. W094/13736 describes the same invention.

U.S. Pat. No. 2,726,526 describes a method of manufacturing a paraffin wax-based candle which has a reduced tendency to drip when burned, which comprises incorporating from about 0.001% to 0.1% by weight of a substituted phenolic compound, e.g., within a substantially non-oxidized melted paraffin wax.

U.S. Pat. No. 3,645,705 teaches a transparent combustible candle body material of an oil and a polyamide. The use of a small amount of an odor-masking agent, stearic acid and 5 percent by weight of an oxidation-inhibiting agent is mentioned.

U.S. Pat. No. 5,171,329 describes a candle comprising of butter oil, flavor, palmitic acid, butylated hydroxyanisole, and solidified oil.

U.S. Pat. No. 5,773,091 teaches a method of treating surfaces to increase resistance of said surfaces to graffiti markings, comprising the steps of applying a coating material to the surface. The coating material is made from water, mineral and synthetic waxes, UV light absorbers, sterically hindered amines, amino ethers and antioxidants.

U.S. Pat. No. 5,879,694 describes a transparent stiff gel candle, comprising a hydrocarbon oil, a wick and one or more triblock, radial block or multiblock copolymer of a thermoplastic rubber, and optionally a diblock copolymer. The candle optionally contains an antioxidant, stabilizer, fragrance, colorant, insect repellant and flame retardant. A specific reference is made to the use of 0.01% by weight of butylated hydroxytoluene as an antioxidant.

U.S. Pat. No. 6,063,144 teaches a substantially non-paraffin candle, comprising a wick and a combustible candle composition consisting essentially of stearic acid, vegetable-derived wax, one vegetable oil, one fragrance, and one oxidation inhibitor. The amount of the oxidation inhibitor in the composition is from 0.01% by weight to 0.5% by weight. The term "substantially non-paraffin" refers to a candle constituted of at least 95% by weight of vegetable or otherwise renewable resources of natural origin and not more than 5% by weight of paraffin or otherwise non-renewable-resource derived materials.

U.S. Pat. No. 6,221,115 describes a candle wax containing a combination of a UV light absorber, preferably a benzotriazole, and a hindered amine. The combination also contains an antioxidant.

U.S. Pat. No. 6,284,007 teaches a candle formed from a vegetable lipid-based composition comprised of a vegetable lipid component and a petroleum wax.

U.S. Pat. No. 6,296,674 describes a white, dyed, dipped, unscented and/or scented candle wax which is effectively stabilized against discoloration and fading by the incorporation therein of a red-shifted benzotriazole either alone or in combination with a hindered amine and/or an antioxidant.

"Peroxide Formation in Aroma Chemicals: The Effect of Chemical Structure and Antioxidants on Product Integrity", an article by Robert H. Bedoukian, teaches the formation of peroxides in many common flavor and fragrance chemicals in the presence of air, and the addition of common antioxidants such as tocopherol and butylated hydroxyanisole to the chemicals for preventing peroxide formation.

It is well known in the art that loss or alteration of candle fragrance during candle manufacture, storage, and burning, is a persistent problem. The solution to this problem has long been sought. Fragrance polymerization can cause attenuation of fragrance release, or alteration of fragrance odor, and it can reduce the size of the candle flame or shut down the capillary flow of wax in the wick and thereby block combustion altogether. The instant composition and method for its preparation provide a solution to this persistent problem.

None of the above references teach the superior protection provided to the candle by the instant composition. The superior protection provided to the candle protects the fragrance from becoming discolored, losing fragrance intensity, or undergoing polymerization. Fragrance polymerization has been shown capable of causing candle tunneling, candle wick clogging, flame attenuation, decreased fragrance intensity, and other undesirable changes which occur during the burning of the candle. The protection of fragrance is also important during the candle manufacturing process, as that process involves heating the wax and fragrance combination.

OBJECTS AND SUMMARY OF THE INVENTION

Surprisingly and unexpectedly it was found that the solubilization of moderate to high levels of antioxidant in the fragrance or in the diluent, which is the same diluent of the fragrance, and then adding this solution to the fragrance and further adding the resulting fragrance containing the dissolved antioxidant to the candle wax blend composition, results in a candle wax composition with outstanding properties. The candle fabricated with the instant candle wax composition, protects the candle from fragrance discoloration, and the other undesirable changes occurring during both candle manufacture and burning.

Thus, it is an object of the invention to provide protection to a fragranced wax candle from the undesirable changes occurring during its manufacture and during the burning of the candle.

It is a more specific object of the invention to provide a fragranced candle wax composition comprising paraffin wax, fragrance containing the dissolved antioxidant, with or without vegetable and/or animal wax, saturated fatty acid, hindered amine, and an additive.

It is another object of the invention to provide a method for incorporating the antioxidant and fragrance into the candle wax composition.

Thus, in one aspect, the present invention provides a fragranced candle wax composition comprising between 10% and 90% of paraffin wax, between 0.1% and 10% by weight of fragrance containing between 0.015% and 2.5% by weight of an antioxidant, with or without 0% to 90% of vegetable wax and/or beeswax, saturated fatty acid, hindered amine, and an additive.

In another aspect, the present invention provides a method for incorporating an antioxidant into the fragranced candle wax composition, said method comprising the steps of: (a) dissolving the antioxidant in the fragrance containing a diluent to form a solution of the fragrance containing the dissolved antioxidant, or alternatively dissolving the antioxidant in an organic diluent which is the same as for the fragrance, and adding the resulting solution of the antioxidant to the fragrance or adding the fragrance to the antioxidant solution to form said fragrance solution, and (b) then subsequently blending said fragrance solution into the molten candle wax to form the fragranced candle wax composition.

The terms used in the present invention are defined below:

The term candle "wax base" refers to the waxy fuel portion of the candle without color or fragrance. Types of candle wax bases include paraffin wax, vegetable wax, beeswax, and very often a combination thereof, such as 50% soy wax, 50% paraffin wax and other additives. The term "burn cycle", as used in test burnings of candles herein, refers to four hours of uninterrupted burning indoors without a breeze. The term "wax pool" refers to the portion of the candle that becomes liquid and remains liquid while the candle burns. This wax pool feeds liquid wax through the wick to the flame via capillary action. The term "pillar candle" refers to a free-standing candle usually three inches in diameter and multiples of three inches in height. These candles are generally designed to burn completely by the end of their life. Pillar candles are generally fabricated from a harder wax base that has a higher melting temperature than many other types of candles. The term "container candle" refers to any candle manufactured in a container in which it will be burned. These containers are usually made of glass, tin or aluminum. Recently, some heat-resistant plastics have been used to fabricate some of these containers. The term "tea light" refers to a small candle manufactured in a cup. The candle measuring approximately 1.5 in. in diameter and 0.75 in. tall is often used to heat potpourri fragrances or as a light source placed on a decorative holder, e.g., a stained glass or cut glass holder.

DETAILED DESCRIPTION OF THE INVENTION

The present invention provides a fragranced wax candle containing different proportions of paraffin wax, fragrance, an antioxidant, optionally vegetable wax and/or beeswax, saturated fatty acid, hindered amine, and an additive. More specifically, the invention provides a fragranced candle wax composition comprising paraffin wax, fragrance containing antioxidant, with or without vegetable and/or beeswax, saturated fatty acid, hindered amine, and an additive. The invention also provides a method for incorporating the fragrance containing the antioxidant into the candle wax composition.

The vegetable wax is hydrogenated vegetable oil and arrayan wax, camauba wax, sugar cane wax, and candelilla wax. The hydrogenated vegetable oil is for example hydrogenated soy oil, hydrogenated castor oil and hydrogenated jojoba oil. The saturated fatty acids are, for example, stearic acid, palmitic acid, and a mixture thereof. The paraffin wax is medium paraffin, and may include microcrystalline wax and other petroleum-based products as for example petrolatum and mineral oil. The melting point of paraffin wax is between 121° F. and 160° F.

The amount of vegetable wax and/or beeswax, saturated fatty acid, hindered amine, and an additive in the candle wax composition is from 0% to 90% by weight and the amount of paraffin wax is approximately 10% to 90% by weight.

The vegetable wax, beeswax, stearic acid, palmitic acid and paraffin wax are commercially available.

The hindered amines useful in the instant invention are well known in the art and are described in detail in U.S. Pat. No. 6,221,115, the relevant parts of which are incorporated herein by reference. Examples of the hindered amines are: 1-(2-hydroxy-2-methylpropoxy)-4-octadecanoyloxy-2,2,6, 6-tetramethylpiperidine; 1-(2-hydroxy-2-methylpropoxy)-4-hydroxy-2,2,6,6-tetramethylpiperidine; bis(1-octyloxy-2, 2,6,6-tetramethylpiperidin-4-yl) sebacate; bis(1-cyclohexyloxy-2,2,6,6-tetramethylpiperidin-4-yl) sebacate; 1-cyclohexyloxy-2,2,6,6-tetramethyl-4-octadecylaminopiperidine; 2,4-bis[(1-cyclohexyloxy-2,2,6,6-tetramethylpiperidin-4-yl)butylamino]-6-(2-hydroxyethylamino-s-triazine; bis(1-cyclohexyloxy-2,2,6,6-tetramethylpiperidin-4-yl) adipate; 1-(2-hydroxy-2-methylpropoxy)-4-oxo-2,2,6,6-tetramethylpiperidine; bis(1-(2-hydroxy-2-methylpropoxy)-2, 2,6,6-tetramethylpiperidin-4-yl) sebacate; bis(1-(2-hydroxy-2-methylpropoxy)-2,2,6,6-tetramethylpiperidin-4-yl) adipate; bis(1-(2-hydroxy-2-methylpropoxy)-2,2,6,6-tetramethylpiperidin-4-yl) succinate; bis(1-(2-hydroxy-2methylpropoxy)-2,2,6,6-tetramethylpiperidin-4-yl) glutarate; and 2,4-bis{N-[1-(2-hydroxy-2-methylpropoxy)-2,2,6,6-tetramethylpiperidin-4-yl]-N-butylamino}-6-(2-hydroxyethylamino)-s-triazine) 1-methoxy-4-hydroxy-2,2,6,6-tetramethylpiperidine; 1-methoxy-4-hydroxy-2,2,6,6-tetramethylpiperidine; 1-octyloxy-4-hydroxy-2,2,6,6-tetramethylpiperidine; 1-cyclohexyloxy-4-hydroxy-2,2,6,6-tetramethylpiperidine; 1-methoxy-4-oxo-2,2,6,6-tetramethylpiperidine; 1-octyloxy-4-oxo-2,2,6,6-tetramethylpiperidine; and 1-cyclohexyloxy-4-oxo-2,2,6,6-tetramethylpiperidine, or a mixture thereof.

The fragrance is a fragrance oil with or without a diluent or a fragrance chemical with or without a diluent; said fragrance can be any natural or synthetic material for use in candles for imparting an odor, aroma, or fragrance. Suitable natural and synthetic fragrance/flavor substances include those listed by the U.S. Food and Drug Administration in Title 21 of the Code of Federal Regulations, Sections 172.510 and 172.515 respectively. Suitable fragrance oils are for example spice oil, flower oil, and fruit oil. Suitable fragrance chemicals are for example benzaldehydes, phenols, cinnamic aldehydes and esters thereof, octadienes, dienes, cyclohexadienes, and terpenes. Suitable fragrance chemicals also include those described Title 21 of the Code of Federal Regulations, Sections 172.510 and 172.515 respectively. The amount of fragrance in the instant composition is from 0.1% to 10% by weight, preferably 4% to 8% by weight, and most preferably 0.5% to 5% by weight. The fragrance is commercially available.

The additive is a colorant such as oil-soluble dyes and pigments that create desired color. Suitable pigments include titanium dioxide and zinc oxide white; copper, bronze, and aluminum metal powders and flakes; and phthalocyanine blue, phthalocyanine green, and yellow and red pigments of the benzimide azolone group such as Pigment Yellow 180 and Pigment Red 208 for colors. For a comprehensive disclosure of pigments and soluble dyes with sufficient thermal stability for use in plastics and therefore also in combustible candle compositions according to this invention, reference can be made to Chapter 63—Organic Colored Pigments (pages 884–899) and Chapter 65—Colors, Dyes (pages 913–919) in "Plastics Additives and Modifiers Handbook", J. Edenbaum (ed.), Van Nostrand Reinhold, N.Y. 1992, herein incorporated by reference. The additives are all commercially available.

The antioxidant is, for example, tertiary butylhydroquinone, n-octadecyl 3,5-di-tert-butyl-4-hydroxyhydrocinnamate, butylated hydroxyanisole, phenol bisphosphite, butylated hydroxytoluene, and phosphite compounds. The antioxidants are all commercially available. An effective amount of antioxidant in the instant composition is 0.015% to 2.5% by weight, preferably 0.1 to 0.75% by weight and most preferably 0.2 to 0.5% by weight of the candle wax.

The fragranced candle wax composition of the instant invention was prepared by combining the various ingredients of the composition, except the fragrance and the dissolved antioxidant, and heating them to form a melt. A separate solution of the antioxidant is prepared by dissolving the antioxidant in a fragrance containing the diluent, or by dissolving the antioxidant in a diluent and then adding the antioxidant solution to the fragrance or adding the fragrance to the antioxidant solution. This solution of fragrance containing the dissolved antioxidant is then added to the melt which is then placed in a suitable mold for the manufacture of the candle. A wick can be placed in the suitable mold surrounded by the melt, or alternatively, a hole can be drilled in the shaped candle after cooling and solidification, and the wick can then be inserted into the hole. Any convenient fiber can be used for the wick, as for example cellulose fibers or cotton. In the case of a glass mold a wick tab has to be attached.

The antioxidant is added according to the following method: a fragrance is dissolved in a diluent to form a solution, and the antioxidant is dissolved in the fragrance solution, or the antioxidant is dissolved in the diluent to form a solution of the antioxidant, and then the solution of the antioxidant is added to the fragrance or the fragrance is added to the antioxidant solution, the resulting solution containing the fragrance and the dissolved antioxidant is then mixed into the molten candle wax.

The diluent is organic, for example: triethyl citrate; di-isopropropyl adipate; di-octyl adipate; isopropyl myristate; isopropyl palmitate; butyl stearate; benzyl alcohol; benzyl benzoate; and diethyl pthalate. The quantity of diluent required is the quantity necessary for dissolving the fragrance or the antioxidant.

As a concentrate for addition to the instant candle wax composition, the antioxidant can be in a powdered, granular, pellet, liquid, gel or tablet form, resulting in a pre-packaged unit dose of the antioxidant. This unit dose of antioxidant can be dissolved in the fragrance containing the diluent or in a diluent which is the same as the diluent for the fragrance, and then adding the solution of the antioxidant to the fragrance, or adding the fragrance to the antioxidant solution and then blending the fragrance solution containing the dissolved antioxidant into the candle wax base.

The candle fabricated with the candle wax composition of the instant invention can be plain, that is, natural, or colored, that is, dyed or pigmented.

A candle fabricated using the antioxidant-protected fragranced candle wax composition of the present invention is superior in terms of preventing the following undesired changes: heat-induced darkening of the fragranced wax, increased viscosity or gelling of the fragrance-containing wax within the melted wax pool surrounding the burning wick, discoloration and formation of a precipitate within the fragrance, reduced flow of molten wax in the wick, and consequently diminished flame intensity and decreasing wax pool temperatures during the burn cycle, as well as diminished fragrance odor intensity. The candle also prevents polymerization, skinning, tunneling and flame attenuation which are due to fragrance within the candle.

EXAMPLES

In order to more clearly describe the subject invention, the following examples are provided for purposes of illustration and are not to be construed as being limiting on the present invention.

Raw Materials

The soy wax was obtained from Cargil Corporation and the paraffin wax was obtained from Exxon corporation. The single-pressed, double-pressed, and the triple-pressed stearic acid were obtained from Cognis Corporation. The fragrances were obtained from the Belmay Corporation. The paraffin wax and microcrystalline wax were obtained from Witco Corporation. and the candle dyes were obtained from Clariant Corporation.

Example 1

Protection of paraffin wax candle containing fragrance and color, using an antioxidant.

(Unprotected Candles)—A candle base wax melt was prepared by melting 50 parts of hydrogenated soy oil (soy wax), 45 parts of paraffin wax and 5 parts of microcrystalline wax. The melt was maintained at 165° F. and then the spice or fruit oil in concentration of 4% to 8% by weight and the solvent red dye were added to the melt, and the mixture was thoroughly stirred. The mixture was then placed in a mold and allowed to cool and the formed candle was retrieved from the mold. This candle when burned exhibited extreme color degradation and darkening. The wax pool which was originally ivory or crème-colored changed to pale orange tan or chocolate brown and the fragrance was discolored. (Protected Candles)—A candle wax melt was prepared using the same procedure as above with the same ingredients and in the same concentrations and maintained at 165° F. A separate solution in a concentration of 0.125% of the antioxidant tertiary butylhydroquinone was prepared by adding the antioxidant to a diluent of di-isopropyl adipate and slowly heating the mixture with magnetic stirring to 80–90° F. After the antioxidant was completely dissolved, the solution was allowed to cool to room temperature and then added to the spice or fruit oil and stirred vigorously. The solution of spice or fruit oil containing the antioxidant was then added to the above candle wax melt at 165° F. and the mixture was thoroughly stirred. Then the mixture was placed in a suitable mold and allowed to cool. The candle was separated from the mold and lighted. This candle upon burning did not show any changes of fragrance, color or wax pool. A second candle was prepared as above except that the candle contained 0.25% concentration of tertiary butylhydroquinone. This candle when burned was most effective in preventing the changes of color, fragrance and wax pool.

Example 2

Protection of paraffin wax candle containing 10% of double-pressed or triple-pressed stearic acid, fragrance and color, using an antioxidant.

(Unprotected Candles)—A candle was prepared as in Example 1, the only difference being that the candle additionally contained 10% of double-pressed or triple-pressed stearic acid. This candle when burned produced the same undesirable changes of color, fragrance and wax pool as in example 1, except that the particular color changes were different.

(Protected Candles)—Two candles were prepared as above except that the candles contained the tertiary butylhydroquinone in concentrations of 0.25% and 0.5%, respectively. The candle prepared with 0.5% of tertiary butylhydroquinone was most effective in preventing changes in color, fragrance and wax pool.

Example 3

Protection of paraffin wax candle with fragrance and color dyes, using a mixture of antioxidants.

(Unprotected Candles) Several candles were prepared as in Example 1 except that the candles were individually colored with red, blue, green, purple, or orange color, or a combination of colors thereof using the corresponding color dyes. The candles when burned showed color and fragrance fading and other degradation.

(Protected Candles) Several candles were prepared as above, except that some candles contained a mixture in concentration of 0.25% of tertiary butylhydroquinone and octadecyl-3,5-di-tertiary butyl-4-hyroxyhydrocinnamate while the other candles contained the same mixture in concentration of 0.5%. Remarkably, when burned these candles prevented color and fragrance fading and degradation.

Example 4

Antioxidant prevention of wax polymerization, tunneling and candlewick clogging in natural wax candles.

(Unprotected Candles) Several candles were prepared as in Example 1. The wax pools of the candles when burned exhibited gelling during burning, and eventually the outer edges of the wax pool became gelatinous and slowed the flow of the wax to the wick. Sometimes, a skin forms over the pool and entirely shuts off the flow of wax to the wick. As wax polymerization continues, the wick becomes clogged and the molten wax pool decreases in diameter. Continued burning and consumption of wax results in a phenomenon known as tunneling. That is, a tunnel is formed down the center of the candle because the candle wax fails to melt outward to the edge of the candle, regardless of whether the candle is a pillar or a container candle.

(Protected Candles) Several candles were prepared as in above except, some candles contained the tertiary butylhydroquinone in concentration of 0.25% while others contained a concentration of 0.5% of the tertiary butylhydroquinone. These candles when burned showed great reduction in the severity of polymerization, skinning, tunneling and flame attenuation.

Example 5

Protection of paraffin wax, double-pressed or triple-pressed stearic acid candles containing fragrance chemicals, from wax discoloration, polymerization and wick clogging during burning, using an antioxidant.

(Unprotected Candles) Candles were prepared as in example 1 except that the candles contained 10% by weight of double- or triple-pressed stearic acid with an iodine value of greater than 0.5 and containing individual fragrance chemicals in concentration of 0.25% by weight, of cinnamic aldehyde, methyl cinnamic aldehyde, eugenol, and limonene. These candles when burned experienced polymerization in the molten wax pool, that is, wax thickening or formation of precipitate in the wax pool, as well as discoloration of the wax pool at various degrees Fahrenheit. The phenomena of polymerization led to wick clogging and flame diminution.

(Protected Candles) Several candles were prepared as above except that the candles contained a concentration of 0.125% or 0.25% of the antioxidant tertiary butylhydroquinone. These candles when burned substantially reduced the incidence and severity of wick shutdown.

Example 6

Protection of polycarbonate candle containers using an antioxidant.

(Unprotected Candles)—Cup tea-light candles were fabricated using the same waxes and fragrance in the same concentrations as Example 1, except that these candles additionally contained 10% by weight of double-pressed or triple-pressed stearic acid and the cups for the candles were manufactured from a plastic material of polycarbonate rather than from aluminum. It was found that the fragrance combined with the waxes caused clouding and cracking of the polycarbonate material within three weeks.

(Protected Candles) Cup tea light candles were fabricated using plastic material of polycarbonate and the same concentrations of components as above except that the candles contained concentrations of 0.1% or 0.2% of the antioxidant tertiary butylhydroquinone. During the period of three weeks, candles with 0.1% tertiary butylhydroquinone showed very little cup deterioration, while the cups holding candles with 0.2% tertiary butylhydroquinone showed no deterioration—that is, they were perfectly clear and showed no cracks.

Example 7

Protection of fragrance odor profile in paraffin wax candle during and after candle burning using an antioxidant.

(Unprotected Candles) Candles were prepared as in Example 1 using the same fragrance and waxes in the same concentrations. During and after a burn cycle these candles exhibited a burnt or acrid smell, especially after the flame was extinguished.

(Protected Candles) Candles were prepared as above except that the candles contained concentrations of 0.1% and 0.2% by weight of tertiary butylhydroquinone. During and after the burn cycle these candles did not exhibit any unpleasant odors, especially after the flame was extinguished.

Example 8

Protection of paraffin wax, double- or triple-pressed stearic acid candles containing fragrance from discoloration, polymerization and wick clogging during burning, using an antioxidant.

(Unprotected Candles) Candles are prepared as in Example 1 except that the candles contain 10% by weight of double- or triple-pressed stearic acid with an iodine value of greater than 0.5 and also contains a spiced or fruit oil in concentration of 5% by weight. These candles upon burning show wax discoloration, polymerization, wick clogging and fragrance discoloration.

(Protected Candles) Several candles are prepared as above except that the candles contain in concentration of 2.5% of the antioxidant tertiary butylhydroquinone. These candles upon burning show no wax discoloration, polymerization, wick clogging or fragrance discoloration.

The invention claimed is:

1. A method of incorporating an antioxidant into a fragranced candle wax composition, comprising the steps of: (a) melting from 10 to 90% by weight of paraffin wax, up to 90% by weight of one or more ingredients selected from the group consisting of vegetable wax, beeswax, saturated fatty acid, hindered amine and an additive, to form a candle wax melt, (b) combining a fragrance, an antioxidant, and optionally, a diluent to form a fragrance solution, and (c) blending said fragrance solution with said candle wax melt to form the fragranced candle wax composition.

2. The method of claim 1, wherein the antioxidant is present in the wax composition from 0.015% to 2.5% by weight of the wax composition.

3. The method of claim 1, wherein the fragrance is a fragrance oil or a fragrance chemical.

* * * * *